United States Patent [19]

Weissmüller et al.

[11] Patent Number: 4,800,202

[45] Date of Patent: Jan. 24, 1989

[54] AMINOMETHYLTETRAHYDROFURANS, FUNGICIDAL COMPOSITIONS AND USE

[75] Inventors: Joachim Weissmüller, Monheim; Dieter Berg, Wuppertal; Stefan Dutzmann, Duesseldorf; Paul Reinecke, Leverkusen, all of Fed. Rep. of Germany

[73] Assignee: Bayer Aktiengesellschaft, Leverkusen, Fed. Rep. of Germany

[21] Appl. No.: 147,416

[22] Filed: Jan. 25, 1988

[30] Foreign Application Priority Data

Feb. 10, 1987 [DE] Fed. Rep. of Germany ....... 3703972
Sep. 11, 1987 [DE] Fed. Rep. of Germany ....... 3730499

[51] Int. Cl.$^4$ ..................... A01N 43/08; A01N 43/84; C07D 307/94; C07D 413/06
[52] U.S. Cl. ..................... 514/227; 424/45; 514/63; 514/212; 514/222; 514/232; 514/234; 514/236; 514/237; 514/239; 514/252; 514/278; 514/373; 514/409; 514/462; 540/543; 544/6; 544/69; 544/70; 546/14; 546/15; 548/211; 548/406; 548/408; 549/214; 549/331
[58] Field of Search ..................... 540/543; 544/6, 70, 544/69; 546/14, 15; 548/211, 406, 408; 549/214, 331; 424/45; 514/63, 212, 227, 232, 234, 236, 237, 239, 252, 278, 373, 409, 462

[56] References Cited

U.S. PATENT DOCUMENTS 3,532,722  10/1970  Belleau et al. .................... 549/331
4,371,538   2/1983  Tsatsas ............................. 549/331

OTHER PUBLICATIONS

Monkovic et al, *Journal of Medicinal Chemistry,* (1973), vol. 16, pp. 403–407.
Mangoni et al, *Chemical Abstracts,* (1963) vol. 59, col. 8567e.

*Primary Examiner*—Robert W. Ramsuer
*Attorney, Agent, or Firm*—Sprung Horn Kramer & Woods

[57] ABSTRACT

Fungicidally active aminomethyltetrahydrofurans of the formula

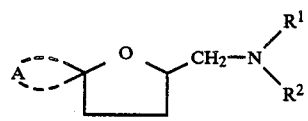

in which
A represents a divalent alkylene or alkenylene chain which is in each case optionally substituted and
$R^1$ and $R^2$ independently of one another each represent hydrogen, alkyl, alkenyl, alkinyl, alkoxyalkyl, dialkoxyalkyl, hydroxyalkyl, hydroxyalkoxyalkyl, dioxolanylalkyl, oxolanylalkyl, or dioxanylalkyl, or represent in each case optionally substituted cycloalkylalkyl, cycloalkyl, aralkyl, aralkenyl or aryl, or
$R^1$ and $R^2$, together with the nitrogen atom to which they are bonded, represent an optionally substituted saturated heterocyclic radical, which can optionally contain further heteroatoms, or an acid addition salts thereof. Some intermediates therefor wherein $NR^1R^2$ is replaced by halogen or sulphonyloxy are also new.

9 Claims, No Drawings

AMINOMETHYLTETRAHYDROFURANS, FUNGICIDAL COMPOSITIONS AND USE

The invention relates to new aminomethyltetrahydrofurans, several processes for their preparation and their use as agents for combating pests.

It is already known that certain aminomethyltetrahydrofurans, such as, for example, 2-(4-chloro-phenyl)-5-(3,5-dimethylpiperidin-1-yl-methyl)-tetrahydrofuran, have fungicidal properties (compare DE-OS (German Published Specification) No. 3,413,996 corresponding to U.S. Pat. No. 4,615,725).

However, the effectiveness of these already known compounds is not completely satisfactory in all fields of use, especially when low amounts are applied and in the case of low concentrations.

New aminomethyltetrahydrofurans of the general formula (I)

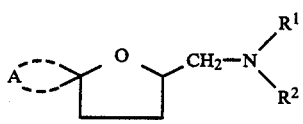

in which
A represents a divalent alkylene or alkenylene chain which is in each case optionally substituted and
$R^1$ and $R^2$ independently of one another each represent hydrogen, alkyl, alkenyl, alkinyl, alkoxyalkyl, dialkoxyalkyl, hydroxyalkyl, hydroxyalkoxyalkyl, dioxolanylalkyl, oxolanylalkyl or dioxanylalkyl, or represent in each case optionally substituted cycloalkylalkyl, cycloalkyl, aralkyl, aralkenyl or aryl, or
$R^1$ and $R^2$, together with the nitrogen atom to which they are bonded, represent an optionally substituted saturated heterocyclic radical, which can optionally contain further heteroatoms, and acid addition salts thereof which are tolerated by plants, have been found.

The compounds of the formula (I) can be in the form of geometric and/or optical isomers or isomer mixtures of various compositions. Both the pure isomers and the isomer mixtures are claimed according to the invention.

It has furthermore been found that the new aminomethyltetrahydrofurans of the general formula (I)

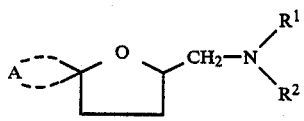

in which
A represents a divalent alkylene or alkenylene chain which is in each case optionally substituted and
$R^1$ and $R^2$ independently of one another each represent hydrogen, alkyl, alkenyl, alkinyl, alkoxyalkyl, dialkoxyalkyl, hydroxyalkyl, hydroxyalkoxyalkyl, dioxolanylalkyl, oxolanylalkyl or dioxanylalkyl, or represent in each case optionally substituted cycloalkylalkyl, cycloalkyl, aralkyl, aralkenyl or aryl, or
$R^1$ and $R^2$, together with the nitrogen atom to which they are bonded, represent an optionally substituted saturated heterocyclic radical, which can optionally contain further heteroatoms,
and acid addition salts thereof which are tolerated by plants, are obtained by a process in which
(a) substituted tetrahydrofurans of the formula (II)

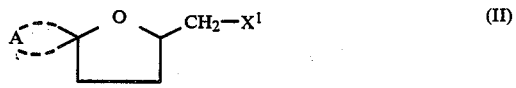

in which
A has the abovementioned meaning and
$X^1$ represents an electron-withdrawing leaving group are reacted with amines of the formula (III)

in which
$R^1$ and $R^2$ have the abovementioned meaning,
if appropriate in the presence of a diluent and if appropriate in the presence of an acid-binding agent, or by a process in which
(b) the aminomethyltetrahydrofurans obtainable by process (a), of the formula (Ia)

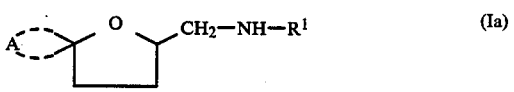

in which
$R^1$ and A have the abovementioned meaning,
are reacted with alkylating agents of the formula (V)

in which
$R^{2-1}$ represents alkyl, alkenyl, alkinyl, alkoxyalkyl, dialkoxyalkyl, hydroxyalkyl, hydroxyalkoxyalkyl, dioxolanylalkyl, oxolanylalkyl or dioxanylalkyl, or represents in each case optionally substituted cycloalkylalkyl, cycloalkyl, aralkyl or aralkenyl and
$X^2$ represents an electron-withdrawing leaving group,
if appropriate in the presence of a diluent and if appropriate in the presence of an acid-binding agent, and if appropriate an acid is then added on.

Finally, it has been found that the new aminomethyltetrahydrofurans of the general formula (I) have an action against pets, in particular against fungal pests.

Surprisingly, the aminomethyltetrahydrofurans of the general formula (I) according to the invention have a better fungicidal activity than the aminomethyltetrahydrofurans known from the prior art, such as, for example, 2-(4-chlorophenyl)-5-(3,5-dimethyl-piperidin-1-yl-methyl)tetrahydrofuran, which are closely related compounds chemically and from the point of view of their action.

Formula (I) provides a general definition of the aminomethyltetrahydrofurans according to the invention. Preferred compounds of the formula (I) are those in which
A represents a divalent alkylene or alkenylene chain which has in each case 3 to 18 carbon atoms and is in each case optionally mono- or polysubstituted by identical or different substituents, possible substituents in each case being: in each case straight-chain or branched alkyl, alkoxy, alkylthio, alkoxycarbonyl, halogenoalkyl, halogenoalkoxy and halogenoalkylthio with in each case 1 to 9 carbon atoms and if appropriate 1 to 9 identical or different halogen atoms; trialkylsilyl with in each case 1 to 4 carbon atoms in the individual straight-chain or branched alkyl parts; cycloalkylalkyl and cycloalkyl which has in each case 3 to 7 carbon atoms in the cycloalkyl part and if appropriate 1 to 4 carbon atoms in the straight-chain or branched alkyl part and is in each case optionally mono- or polysubstituted by identical or different substituents from the group comprising alkyl with 1 to 4 carbon atoms and/or halogen; in each case divalent alkylene or alkenylene which has in each case up to 5 carbon atoms and is in each case optionally mono- or polysubstituted by identical or different substituents from the group comprising alkyl, halogenoalkyl, alkoxy and halogenoalkoxy with in each case 1 to 4 carbon atoms and if appropriate 1 to 9 identical or different halogen atoms and/or halogen, and monovalent aryl or divalent arylene which has in each case 6 to 10 carbon atoms and is in each case optionally mono- or polysubstituted by identical or different substituents, possible substituents in each case being: halogen, cyano, nitro and in each case straight-chain or branched alkyl, alkoxy, alkylthio, halogenoalkyl, halogenoalkoxy, halogenoalkylthio, alkoxycarbonyl and alkoximinoalkyl with in each case 1 to 4 carbon atoms in the individual alkyl parts and if appropriate 1 to 9 identical or different halogen atoms, and $R^1$ and $R^2$ independently of one another each represent hydrogen; or represent in each case straight-chain or branched alkyl with 1 to 12 carbon atoms, alkenyl with 3 to 8 carbon atoms, alkinyl with 3 to 8 carbon atoms, hydroxyalkyl with 2 to 6 carbon atoms, alkoxyalkyl or dialkoxyalkyl with in each case 1 to 6 carbon atoms or hydroxyalkoxyalkyl with 2 to 6 carbon atoms in the individual alkyl parts, or represent in each case straight-chain or branched dioxolanylalkyl, oxolanylalkyl, or dioxanylalkyl with in each case 1 to 4 carbon atoms in the alkyl part, or represent cycloalkyl or cycloalkylalkyl which has in each case 3 to 7 carbon atoms in the cycloalkyl part and if appropriate 1 to 4 carbon atoms in the alkyl part and is in each case optionally mono- or polysubstituted by identical or different substituents in the cycloalkyl part, possible substituents in each case being: halogen and in each case straight-chain or branched alkyl, alkoxy, halogenoalkyl and halogenoalkoxy with in each case 1 to 4 carbon atoms and if appropriate 1 to 9 identical or different halogen atoms; or furthermore represent arylalkyl, arylalkenyl or aryl which has in each case 6 to 10 carbon atoms in the aryl part and if appropriate up to 6 carbon atoms in the straight-chain or branched alkyl or alkenyl part and is in each case optionally mono- or polysubstituted by identical or different substituents in the aryl part, possible substituents on the aryl in each case being: halogen, cyano, nitro and in each case straight-chain or branched alkyl, alkoxy, alkylthio, halogenoalkyl, halogenoalkoxy, halogenoalkylthio, alkoxycarbonyl and alkoximinoalkyl with in each case 1 to 4 carbon atoms in the individual alkyl parts and if appropriate 1 to 9 identical or different halogen atoms, or $R^1$ and $R^2$, together with the nitrogen atom to which they are bonded, represent a saturated 5- to 7-membered heterocyclic radical which is optionally mono- or polysubstituted by identical or different substituents and can optionally contain a further heteroatom, in particular nitrogen, oxygen or sulphur, possible substituents being: in each case straight-chain or branched alkyl and hydroxyalkyl with in each case 1 to 4 carbon atoms.

Particularly preferred compounds of the formula (I) are those in which

A represents, 1,4-butylene, 1,5-pentylene, 1,6-hexylene, 1,5-pent-1-enylene, 1,5-pent-2-enylene or 1,11-undecylene, in each case optionally mono-, di-, tri-, tetra- or pentasubstituted by identical or different substituents, possible substituents in each case being: methyl, ethyl, n- or i-propyl, n-, i-, s- or t-butyl, n- or i-pentyl, n- or i-hexyl, n- or i-heptyl, n- or i-octyl, n- or i-nonyl, methoxy, ethoxy, n- or i-propoxy, n-, i-, s- or t-butoxy, methylthio, methoxycarbonyl, ethoxycarbonyl, trifluoromethyl, trifluoromethoxy, trifluoromethylthio and trimethylsilyl, cyclohexyl, cyclohexylmethyl, cyclohexylethyl and cyclohexylpropyl, in each case optionally mono, di- or trisubstituted by identical or different substituents from the group comprising fluorine, chlorine, bromine, methyl, ethyl, n- or i-propyl and/or t-butyl, methylene, 1,2-ethylene, 1,3-propylene, 1,4-butylene and 1,4-butenylene, in each case optionally mono-, di- or trisubstituted by identical or different substituents from the group comprising methyl, ethyl, n- or i-propyl, n-, i-, s- or t-butyl, trifluoromethyl and/or trifluoromethoxy, and phenyl and o-phenylene, in each case optionally mono-, di- or trisubstituted by identical or different substituents, possible substituents in each case being: fluorine, chlorine, bromine, cyano, nitro, methyl, ethyl, n- or i-propyl, n-, i-, s- or t-butyl, methoxy, ethoxy, trifluoromethyl, trifluoromethoxy, trifluoromethylthio and methoximinomethyl, and $R^1$ and $R^2$ independently of one another each represent hydrogen, methyl, ethyl, n- or i-propyl, n-, i-, s- or t-butyl, n- or i-pentyl, n- or i-hexyl, n- or i-heptyl, n- or i-octyl, allyl, n- or i-butenyl, n- or i-pentenyl, propargyl, n- or i-butinyl, hydroxyethyl, hydroxypropyl, methoxyethyl, ethoxyethyl, propoxyethyl, butoxyethyl, methoxypropyl, ethoxypropyl, propoxypropyl, butoxypropyl, hydroxyethoxyethyl, dimethoxyethyl, dimethoxypropyl, diethoxyethyl, dioxolanylmethyl, dioxolanylethyl, dioxanylmethyl, dioxanylethyl or oxolanylmethyl or oxolanylethyl, or represent cyclopropyl, cylopropylmethyl, cyclopropylethyl, cyclopropylpropyl, cyclopentyl, cyclopentylmethyl, cyclohexyl or cyclohexylmethyl, in each case optionally mono-, di-, tri-, tetra- or pentasubstituted by identical or different substituents from the group comprising fluorine, chlorine, bromine, methyl ethyl, n- or i-propyl and n-, i-, s- and/or t-butyl, or represent phenyl, benzyl or phenethyl, in each case optionally mono-, di- or trisubstituted by identical or different substituents, possible substituents in each case being: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy, trifluoromethylthio, methoxycarbonyl, ethoxycarbonyl and methoximinomethyl, or R¹ and R², together with the nitrogen atom to which they are bonded, represent a heterocyclic radical of the formula

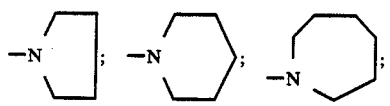

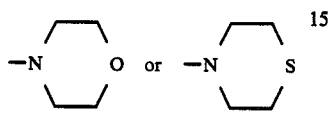

which is optionally mono-, di- or trisubstituted by identical or different substituents, possible substituents being: methyl, ethyl and hydroxymethyl.

Especially preferred compounds of the formula (I) are those in which

A, together with the carbon atom to which it is bonded, represents a carbocyclic ring system of the formula

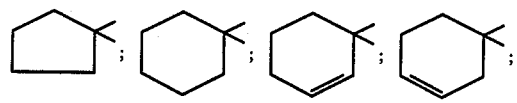

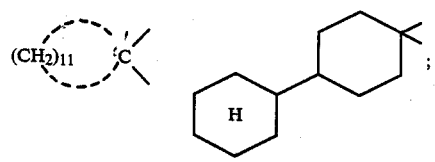

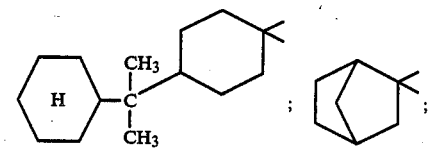

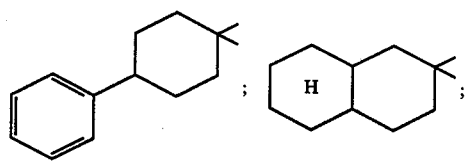

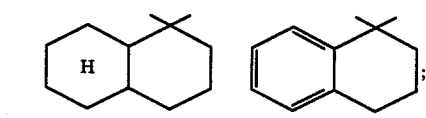

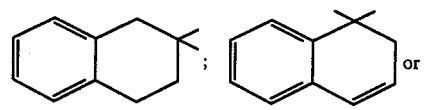

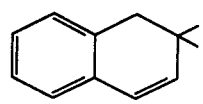

which is optionally mono-, di or trisubstituted by identical or different substituents, possible substituents in the cycloaliphatic rings in each case being: methyl, ethyl, n- or i-propyl, n-, i-, s- or t-butyl, n- or i-pentyl, trifluoromethyl, trifluoromethoxy, methoxycarbonyl, ethoxycarbonyl and trimethylsilyl, and possible substituents in the aromatic rings in each case being: fluorine, chlorine, bromine, methyl, ethyl, n- or i-propyl, n-, i-, s- or t-butyl, methoxy, ethoxy, trifluoromethyl, trifluoromethoxy and trifluoromethylthio, and R¹ and R² independently of one another each represent hydrogen, methyl, ethyl, n- or i-propyl, n-, i-, s- or t-butyl, n- or i-pentyl, n- or i-hexyl, allyl, n- or i-butenyl, n- or i-pentenyl, propargyl, n- or i-butinyl, hydroxyethyl, hydroxypropyl, methoxyethyl, methoxypropyl, ethoxyethyl, ethoxypropyl, hydroxyethoxyethyl, dimethoxyethyl, diethoxyethyl, dioxolanylmethyl, dioxolanylethyl, oxolanylmethyl, oxolanylethyl, dioxanylmethyl, cyclopropylmethyl, dichlorocyclopropylmethyl, dimethylcyclopropylmethyl, dichlorodimethylcyclopropylmethyl, cyclopentyl, cyclohexyl or cyclohexylmethyl, or R¹ and R², together with the nitrogen atom to which they are bonded, represent a heterocyclic radical of the formula

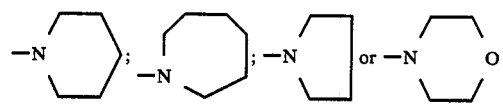

which is optionally mono-, di- or trisubstituted by identical or different substituents, possible substituents being: methyl, ethyl and hydroxymethyl.

Addition products of acids and those aminomethyltetrahydrofurans of the formula (I) in which the substituents A, R¹ and R² have the meanings which have already been mentioned for these substituents are also preferred compounds according to the invention.

The acids which can be added on preferably include hydrogen halide acids, such as, for example, hydrochloric acid and hydrobromic acid, in particular hydrochloric acid, and furthermore phosphoric acid, nitric acid, mono-, di- and trifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as p-toluenesulphonic acid and 1,5-naphthalenedisulphonic acid, as well as saccharine.

The following aminomethyltetrahydrofurans of the general formula (I) may be mentioned specifically, in addition to the compounds mentioned in the preparation examples:

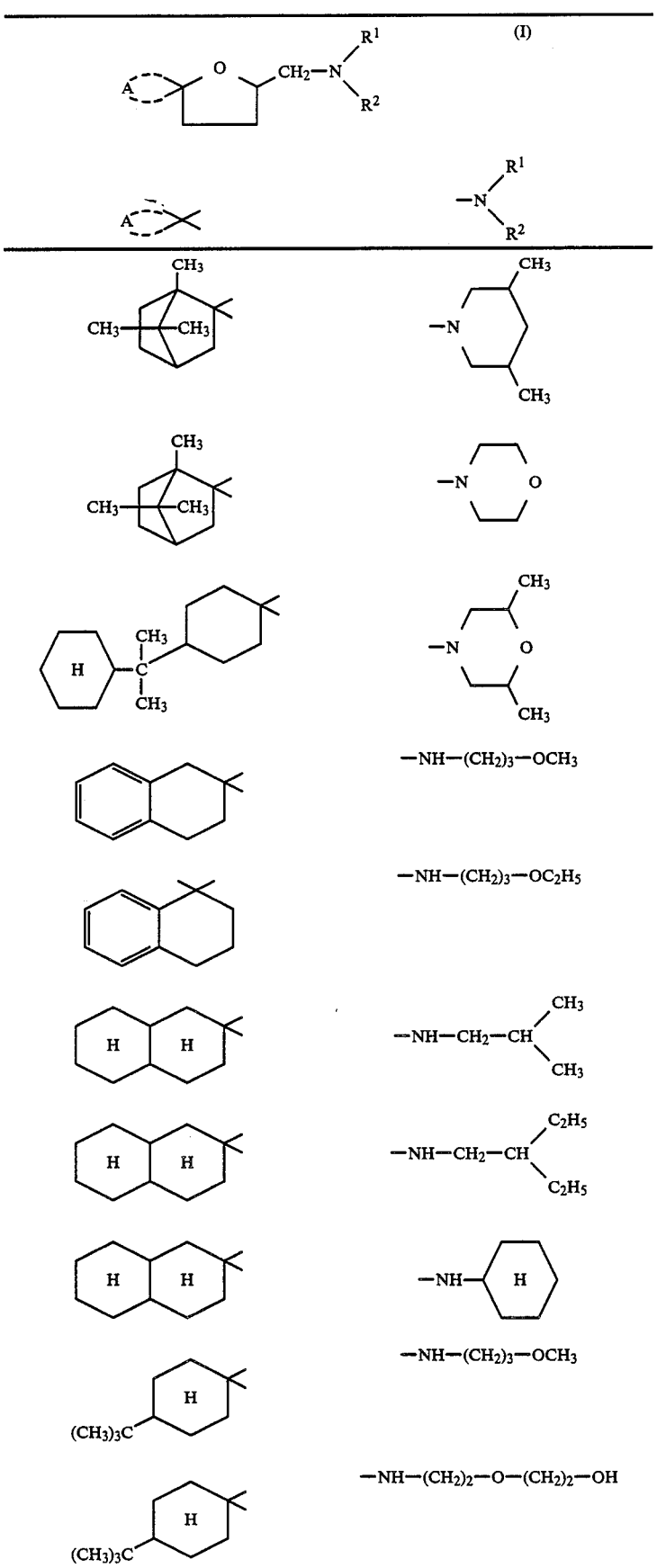

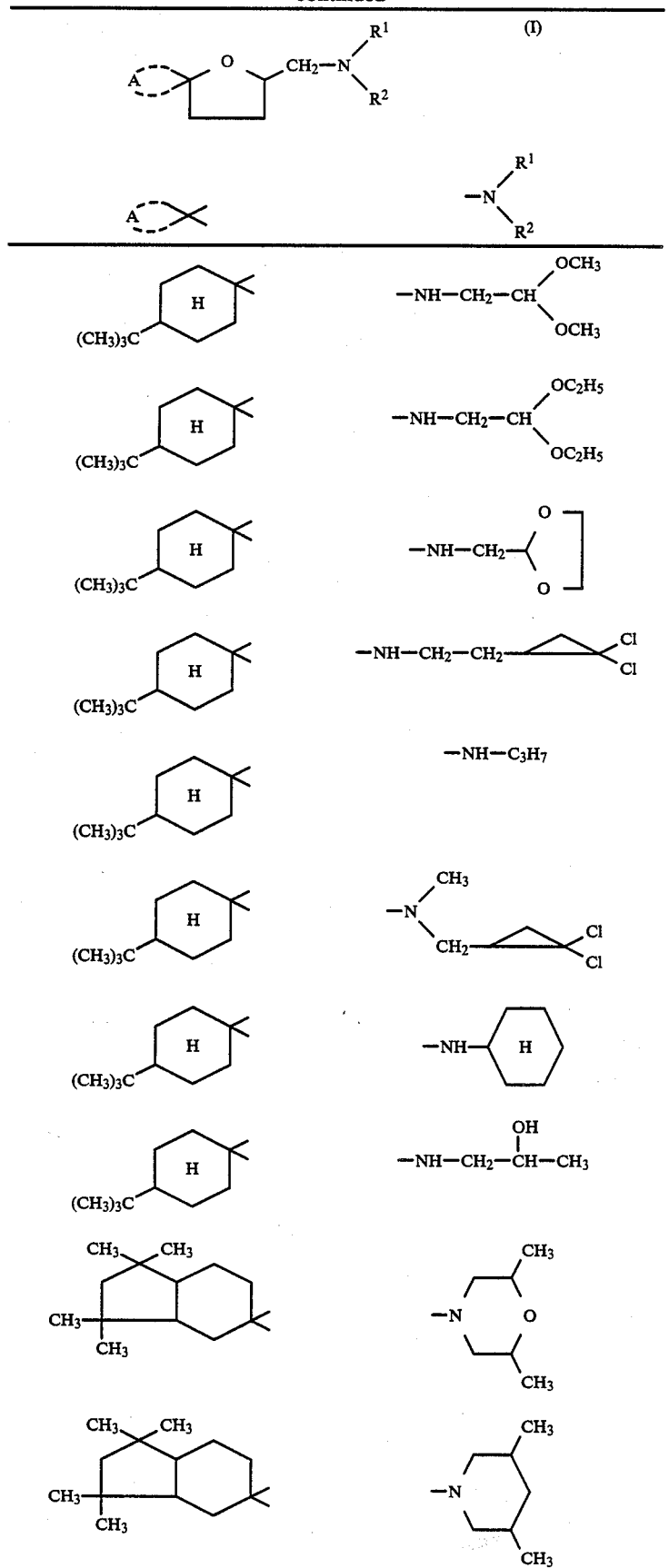

-continued
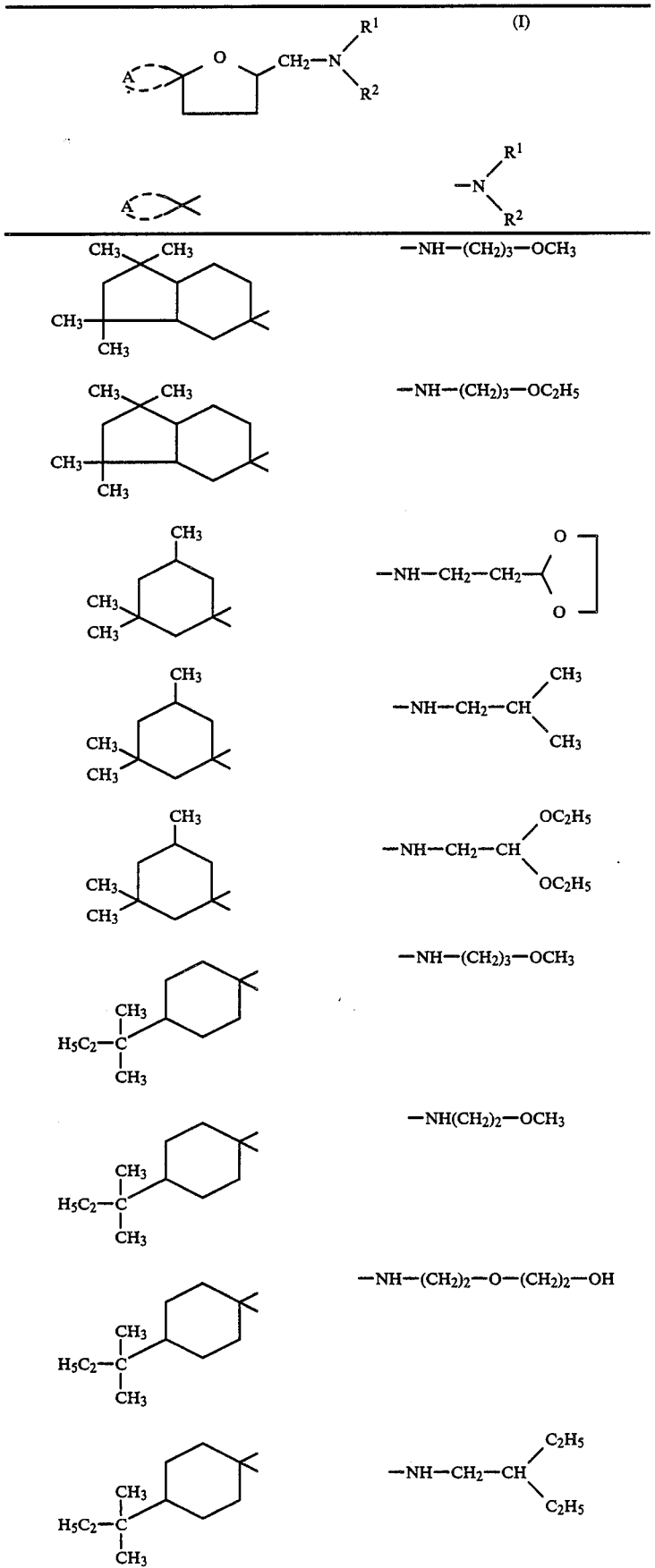

-continued
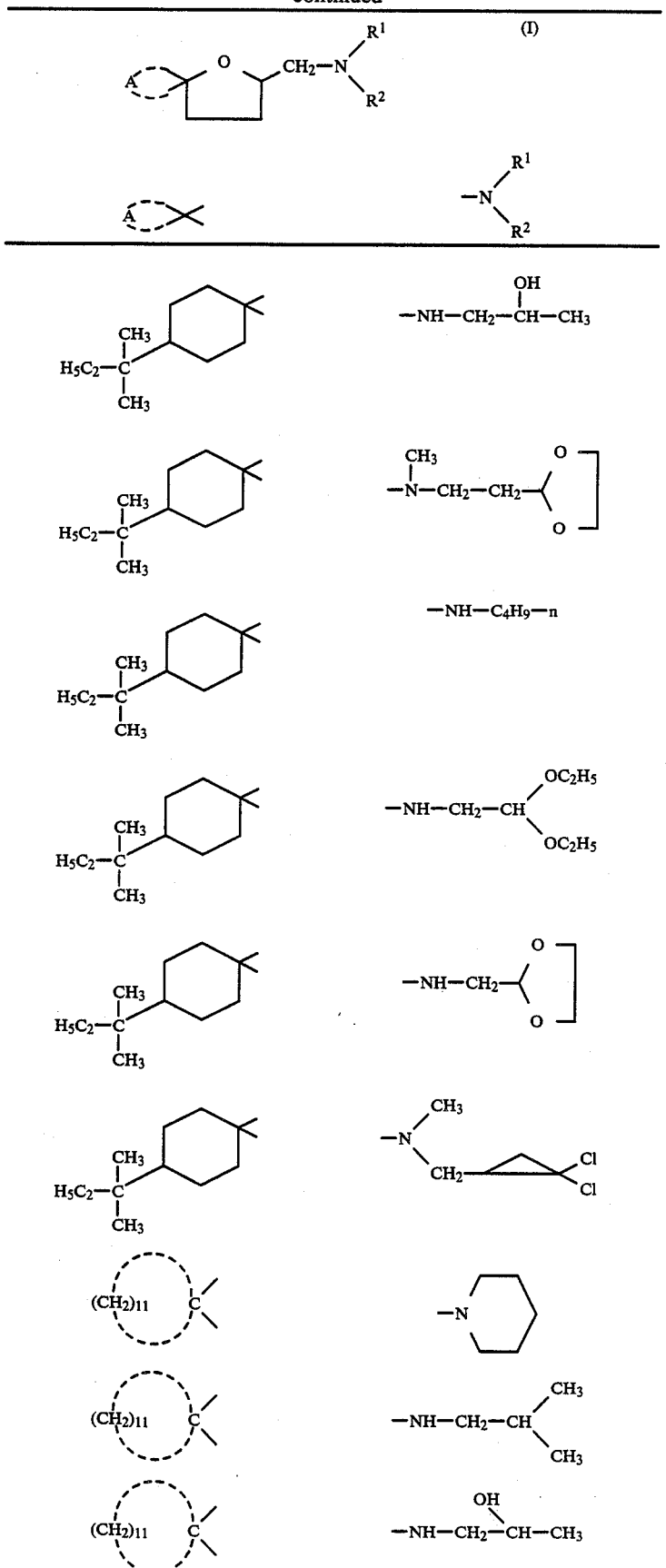

-continued
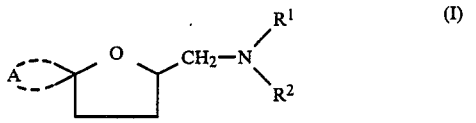 (I)
| A |  |
|---|---|
|  | —NH—(CH$_2$)$_2$—OCH$_3$ |
| 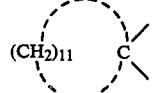 | —NH—(CH$_2$)$_2$—O—(CH$_2$)$_2$—OH |
| 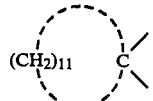 | 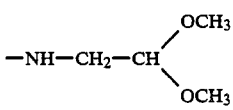 |
| 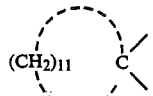 | —NH—C$_3$H$_7$—n |
| 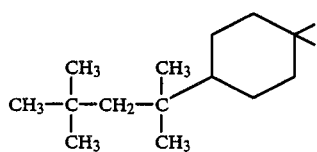 | 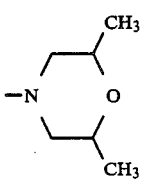 |
| 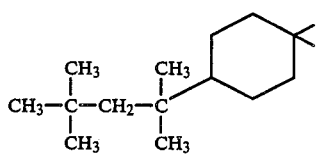 | 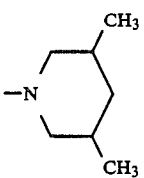 |
| 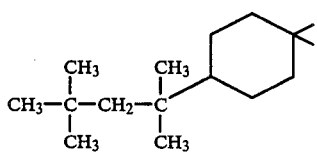 | 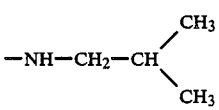 |
| 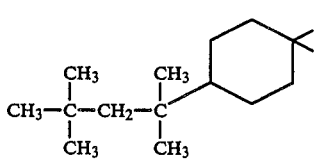 | —NH—(CH$_2$)$_3$—OC$_2$H$_5$ |
| 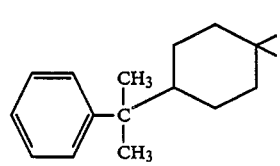 | 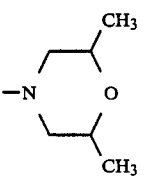 |

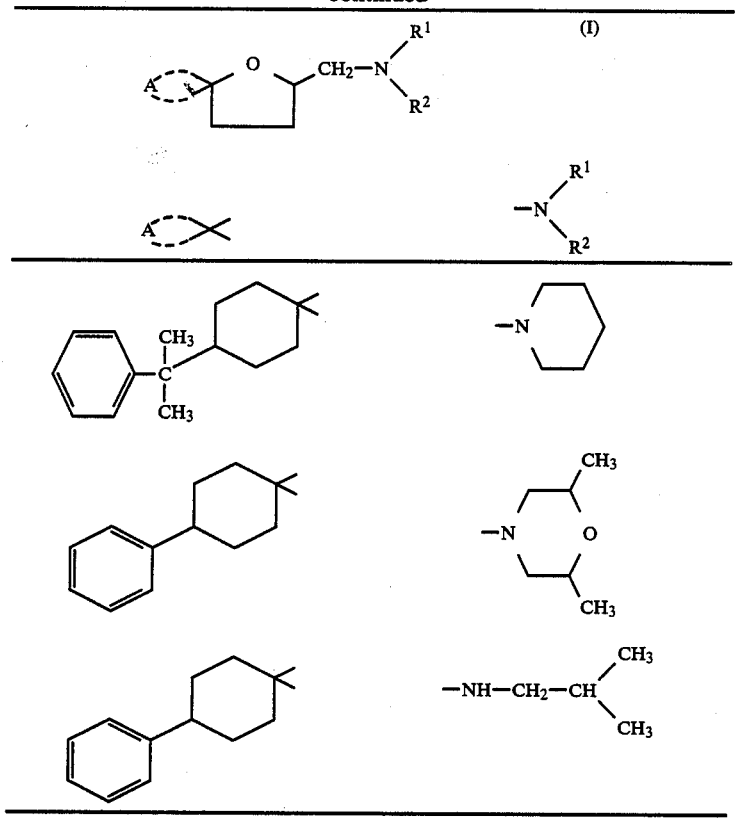

If, for example, 2-bromomethyl-1-oxaspiro[4,5]decane and piperidine are used as starting substances, the course of the reaction in process (a) according to the invention can be represented by the following equation:

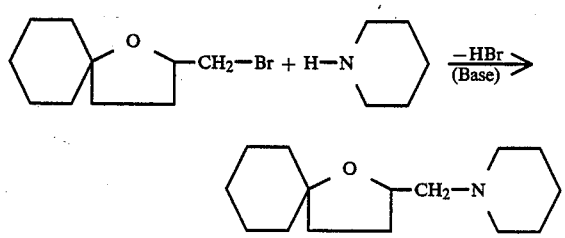

If, for example, 8-t-butyl-2-(N-cyclohexylaminomethyl)-1-oxaspiro[4,5]decane and allyl bromide are used as starting substances, the course of the reaction in process (b) according to the invention can be represented by the following equation:

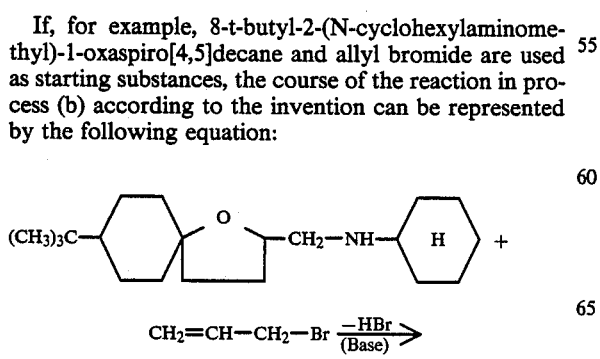

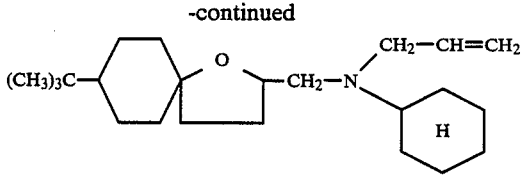

Formula (II) provides a general definition of the substituted tetrahydrofurans required as starting substances for carrying out process (a) according to the invention. In this formula (II), A preferably represents those radicals which have already been mentioned as preferred for these substituents in connection with the description of the substances of the formula (I) according to the invention.

$X^1$ preferably represents halogen, in particular chlorine or bromine, or represents optionally substituted alkylsulphonyloxy with 1 to 4 carbon atoms, or arylsulphonyloxy which is optionally mono- or polysubstituted by alkyl with 1 to 4 carbon atoms, such as, for example, methanesulphonyloxy or p-toluenesulphonyloxy.

The substituted tetrahydrofurans of the formula (II) are known in some cases (compare, for example, Heterocycles 23, 2035–2039 [1985]).

Compounds which are not yet known are the substituted tetrahydrofurans of the formula (IIa)

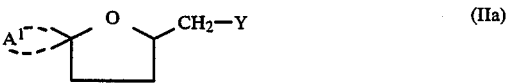

(IIa)

in which
- $A^1$ represents a divalent alkylene or alkenylene chain which is in each case optionally substituted and
- Y represents halogen, or represents in each case optionally substituted alkylsulphonyloxy or arylsulphonyloxy, with the exception of the compounds in which $A^1$ represents a 1,4-butanediyl chain and at the same time Y represents bromine or iodine.

The alkylsulphonyloxy radical can contain 1 to 4 carbon atoms and can be optionally mono- or polysubstituted by halogen, and the arylsulphonyloxy radical preferably represents a phenylsulphonyloxy radical which is optionally substituted by alkyl with 1 to 4 carbon atoms.

The substituted tetrahydrofurans of the formula (IIa) which are not yet known can be prepared by processes analogous to known processes (compare, for example, DE-OS (German Published Specification) No. 3,413,996), for example by a procedure in which the generally known cyclic ketones of the formula (VI)

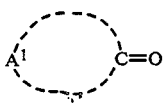
(VI)

in which
- $A^1$ has the abovementioned meaning, are initially reacted in a first stage with buten-1-yl-4-magnesium bromide of the formula (VII)

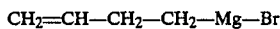
$$CH_2=CH-CH_2-CH_2-Mg-Br \quad (VII)$$

in the presence of a diluent, such as, for example, diethyl ether or tetrahydrofuran, at temperatures between −20° C. and +50° C. (in this context, compare also Tetrahedron Lett. 26, 127–130 [1985]; Bull. Soc. Chim. Fr. 12, Pt. 2, 3377–3381 [1973] or the Preparation Examples), and the carbinols thus obtainable, of the formula (VIII)

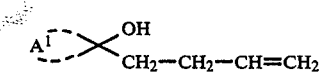
(VIII)

in which
- $A^1$ has the abovementioned meaning, are reacted with a halogenating agent, such as, for example, elemental bromine, in the presence of quinoline or with N-bromosuccinimide, if appropriate in the presence of a diluent, such as, for example, chloroform, at temperatures between −20° C. and +80° C. (in this context, compare alse DE-OS (German Published Specification) No. 3,413,996), or by a procedure in which trihydroxy compounds of the formula (IX)

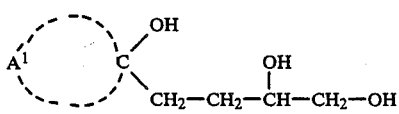
(IX)

in which
- $A^1$ has the abovementioned meaning, are cyclized with acids, such as, for example, sulphuric acid or phosphoric acid, in the customary manner (compare, for example, Houben-Weyl, "Methoden der organischen Chemie" ("Methods of Organic Chemistry"), Volume VI/3 page 528; 4th edition, Thieme Verlag Stuttgart or Khim. Geterotsikl. Soedin. Sb. No. 2, 15–17, [1970] and C.A. 77, 48144 g), and the hydroxymethyltetrahydrofurans thus obtainable, of the formula (X)

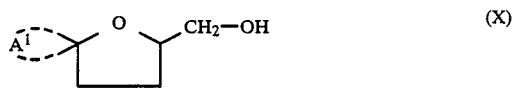
(X)

in which
- $A^1$ has the abovementioned meaning, are reacted in a 2nd stage with sulphonic acid halides of the formula (XI)

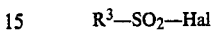
$$R^3-SO_2-Hal \quad (XI)$$

in which
- $R^3$ represents alkyl which is optionally substituted by halogen or aryl which is optionally substitured by alkyl with 1 to 4 carbon atoms, in particular methyl, trifluoromethyl or p-tolyl, and
- Hal represents halogen, in particular chlorine, bromine or iodine, if appropriate in the presence of a diluent, such as, for example, methylene chloride, and if appropriate in the presence of an acid-binding agent, such as, for example, pyridine, at temperatures between 0° and 120° C.

Alternatively, the carbinols of the formula (VIII) are also obtained by a process in which the ketones of the formula (VI) are epoxidized in a manner which is known in principle, for example with a trimethylsulphonium ylide, and the products are then reacted with allylmagnesium bromide (compare, for example, J. Am. Chem. Soc. 87, 1363–1364 [1965] or Heterocycles 8, 397 [1977]).

The sulphonic acid halides of the formula (XI) are generally known compounds of organic chemistry.

The trihydroxy compounds of the formula (IX) are known or are obtainable by processes analogous to known processes (compare, for example, Bull. Soc. Chim. France 1964, 564–569; Belgian Pat. No. 631,243 of Nov. 4, 1963; Belgian Pat. No. 631,242 of Nov. 4, 1963; British Pat. No. 1,036,087 of July 13, 1966 or French Pat. No. 1,334,968 of Aug. 16, 1963.

Formula (III) provides a general definition of the amines furthermore required as starting substances for carrying out process (a) according to the invention. In this formula (III), $R^1$ and $R^2$ preferably represent those radicals which have already been mentioned as preferred for these substituents in connection with the description of the substances of the formula (I) according to the invention.

The amines of the formula (III) are generally known compounds of organic chemistry.

Formula (Ia) provides a general definition of the aminomethyltetrahydrofurans required as starting substances for carrying out process (b) according to the invention. In this formula (Ia), A and $R^1$ preferably represent those radicals which have already been mentioned as preferred for these substituents in connection with the description of the substances of the formula (I) according to the invention.

The aminomethyltetrahydrofurans of the formula (Ia) are compounds according to the invention and are obtainable with the aid of process (a) according to the invention.

Formula (V) provides a general definition of the alkylating agents furthermore required as starting substances for carrying out process (b) according to the invention. In this formula (V), $R^{2-1}$ preferably represents in each case straight-chain or branched alkyl with 1 to 12 carbon atoms, alkenyl with 3 to 8 carbon atoms, alkinyl with 3 to 8 carbon atoms, hydroxyalkyl with 2 to 6 carbon atoms, alkoxyalkyl or dialkoxyalkyl with in each case 1 to 6 carbon atoms or hydroxyalkoxyalkyl with 2 to 6 carbon atoms in the individual alkyl parts; or represent in each case straightchain or branched dioxolanylalkyl, oxolanylalkyl or dioxanylalkyl with in each case 1 to 4 carbon atoms in the alkyl part; or represent cycloalkyl or cycloalkylalkyl which has in each case 3 to 7 carbon atoms in the cycloalkyl part and if appropriate 1 to 4 carbon atoms in the alkyl part and is in each case optionally mono- or polysubstituted by identical or different substituents in the cycloalkyl part, possible substituents in each case being: halogen and in each case straight-chain or branched alkyl, alkoxy, halogenoalkyl and halogenoalkoxy with in each case 1 to 4 carbon atoms and if appropriate 1 to 9 identical or different halogen atoms; or furthermore represent arylalkyl or arylalkenyl which has in each case 6 to 10 carbon atoms in the aryl part and up to 6 carbon atoms in the straight-chain or branched alkyl or alkenyl part and is in each case optionally mono- or polysubstituted by identical or different substituents in the aryl part, possible substituents of the aryl in each case being: halogen, cyano, nitro, and in each case straight-chain or branched alkyl, alkoxy, alkylthio, halogenoalkyl, halogenoalkoxy, halogenoalkylthio, alkoxycarbonyl and alkoximinoalkyl with in each case 1 to 4 carbon atoms in the individual alkyl parts and if appropriate 1 to 9 identical or different halogen atoms.

$R^{2-1}$ particularly preferably represents methyl, ethyl, n- or i-propyl, n-, i-, s- or t-butyl, n- or i-pentyl, n- or i-hexyl, n- or i-heptyl, n- or i-octyl, allyl, n- or i-butenyl, n- or i-pentenyl, propargyl, n- or i-butinyl, hydroxyethyl, hydroxypropyl, methoxyethyl, ethoxyethyl, propoxyethyl, butoxyethyl, methoxypropyl, ethoxypropyl, propoxypropyl, butoxypropyl, hydroxyethoxyethyl, dimethoxyethyl, dimethoxypropyl, diethoxyethyl, dioxolanylmethyl, dioxolanylethyl, oxolanylmethyl, oxolanylethyl, dioxanylmethyl or dioxanylethyl, or represents cyclopropyl, cyclopropylmethyl, cyclopropylethyl, cyclopropylpropyl, cyclopentyl, cyclopentylmethyl, cyclohexyl or cyclohexylmethyl, in each case optionally mono-, di-, tri-, tetra- or pentasubstituted by identical or different substituents from the group comprising fluorine, chlorine, bromine, methyl, ethyl, n- or i-propyl and n-, i-, s- and/or t-butyl, or represent benzyl or phenethyl, in each case optionally mono-, di- or trisubstituted by identical or different substituents, possible substituents in each case being: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy, trifluoromethylthio, methoxycarbonyl, ethoxycarbonyl or methoximinomethyl.

$R^{2-1}$ especially preferably represents methyl, ethyl, n- or i-propyl, n-, i-, s- or t-butyl, n- or i-pentyl, n- or i-hexyl, allyl, n- or i-butenyl, n- or i-pentenyl, propargyl, n- or i-butinyl, hydroxyethyl, hydroxypropyl, methoxyethyl, methoxypropyl, ethoxyethyl, ethoxypropyl, hydroxyethoxyethyl, dimethoxyethyl, diethoxyethyl, dioxolanylmethyl, dioxolanylethyl, oxolanylmethyl, oxolanylethyl, dioxanylmethyl, cyclopropylmethyl, dichlorocyclopropylmethyl, dimethylcyclopropylmethyl, dichlorodimethylcyclopropylmethyl, cyclopentyl, cyclohexyl or cyclohexylmethyl.

$X^2$ preferably represents halogen, in particular chlorine, bromine or iodine, or represents in each case optionally halogen-substituted alkylsulphonyloxy, or alkoxysulphonyloxy with in each case 1 to 4 carbon atoms and if appropriate 1 to 9 halogen atoms or arylsulphonyloxy which is optionally substituted by alkyl with 1 to 4 carbon atoms, such as, for example, methanesulphonyloxy, methoxysulphonyloxy or p-toluenesulphonyloxy.

The alkylating agents of the formula (V) are likewise generally known compounds of organic chemistry or are obtainable by processes analogous to generally known processes.

Possible diluents for carrying out processes (a) and (b) according to the invention are inert organic solvents or aqueous systems. These include, in particular, aliphatic or aromatic, optionally halogenated hydrocarbons, such as, for example, benzine, benzene, toluene, xylene, chlorobenzene, petroleum ether, hexane, cyclohexane, methylene chloride, chloroform or carbon tetrachloride; ethers, such as diethyl ether, dioxane, tetrahydrofuran or ethylene glycol dimethyl or diethyl ether; ketones, such as acetone or butanone; nitriles, such as acetonitrile or propionitrile; amides, such as dimethylformamide, dimethylacetamide, N-methylformanilide, N-methylpyrrolidone or hexamethylphosphoric acid triamide; esters, such as ethyl acetate, or sulphoxides, such as dimethyl sulphoxide.

If appropriate, processes (a) and (b) according to the invention can also be carried out in a two-phase system, such as, for example, water/toluene or water/methylene chloride, if appropriate in the presence of a phase transfer catalyst. Examples of such catalysts which may be mentioned are: tetrabutylammonium iodide, tetrabutylammonium bromide, tributyl-methylphosphonium bromide, trimethyl-$C_{13}/C_{15}$-alkylammonium chloride, dibenzyldimethyl-ammonium methylsulphate, dimethyl-$C_{12}/C_{14}$-alkylbenzylammonium chloride, tetrabutylammonium hydroxide, 15-crown-5, 18-crown-6, triethylbenzylammonium chloride, and trimethylbenzylammonium chloride. It is also possible for processes (a) and (b) according to the invention to be carried out without the addition of a solvent.

Possible acid-binding agents for carrying out processes (a) and (b) according to the invention are all the inorganic and organic bases which can usually be employed. Bases which are preferably used are alkali metal hydroxides, carbonates or bicarbonates, such as, for example, sodium hydroxide, sodium carbonate or sodium bicarbonate, or tertiary amines, such as, for example, triethylamine, N,N-dimethylaniline, pyridine, 4-(N,N-dimethylamino)pyridine, diazabicyclooctane (DABCO), diazabicyclononene (DBN) or diazabicycloundecene (DBU).

It is also possible for the amines of the formulae (III) and (Ia) used as participants in the reaction to be simultaneously employed in an appropriate excess as the acid-binding agent.

The reaction temperatures can be varied within a substantial range in carrying out processes (a) and (b) according to the invention. The reaction is in general carried out at temperatures between −20° C. and +180° C., preferably at temperatures between 20° C. and +150° C.

For carrying out process (a) according to the invention, in general 1.0 to 3.0 mols, preferably 1.0 to 1.5 mols, of amine of the formula (III) and if appropriate 1.0 to 3.0 mols, preferably 1.0 to 1.5 mols, of acid-binding agent, and if appropriate 0.1 to 1.0 mol of phase transfer catalyst are employed per mol of substituted tetrahydrofuran of the formula (II).

For carrying out process (b) according to the invention, in general 1.0 to 5.0 mols, preferably 1.0 to 2.0 mols, of alkylating agent of the formula (V) and 1.0 to 5.0 mols, preferably 1.0 to 2.0 mols, of acid-binding agent and if appropriate 0.1 to 1.0 mol of phase transfer catalyst are employed per mol of aminomethyltetrahydrofuran of the formula (Ia).

The reaction is carried out and the reaction products of the formula (I) are worked up and isolated in both cases by customary methods.

The following acids can preferably be used for the preparation of acid addition salts of the compounds of the formula (I): hydrogen halide acids, such as, for example, hydrochloric acid and hydrobromic acid, in particular hydrochloric acid, and furthermore phosphoric acid, nitric acid, sulphuric acid, mono-, di- and trifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and 1,5-naphthalenedisulphonic acid, as well as saccharine.

The acid addition salts of the compounds of the formula (I) can be obtained in a simple manner by customary salt formation methods, such as, for example, by dissolving a compound of the formula (I) in a suitable inert solvent and adding the acid, such as, for example, hydrochloric acid, and they can be isolated in a known manner, for example by filtration, and if appropriate purified by washing in an inert organic solvent.

The active compounds according to the invention exhibit a powerful action against pests and can be used in practice for combating undesirable harmful organisms. The active compounds are suitable for use, inter alia, as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation: Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubensis;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptospaeria nodorum;* Cercospora species, such as, for example, *Cercospora canescens;* Alternaria species, such as, for example, *Alternaria brassicae* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention can be used with particularly good success here for combating cereal diseases, such as, for example, against the powdery mildew of barley causative organism (*Erysiphe graminis*) or against the brown spot of wheat causative organism (*Leptosphaeria nodorum*), for combating rice diseases, such as, for example, against the leaf spot disease of rice causative organism (*Pyricularia oryzae*), or for combating diseases in fruit- and vegetable-growing, such as, for example, against the apple scab causative organism (*Venturia inaequalis*).

Depending on their particular physical and/or chemical properties, the active compounds can be converted to the customary formulations, such as solutions, emulsions, suspensions, powders, foams, pastes, granules, aerosols, natural and synthetic material impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surfaceactive agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and growth regulators.

The active compounds can be used as such or in the form of their formulations or the use forms prepared therefrom, such as ready-to-use solutions, supsensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

Preparation Examples

Example 1

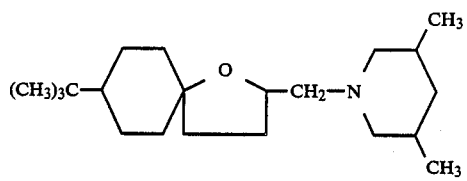

(Process a)

A mixture of 15 g (0.05 mol) of 2-bromomethyl-8-t-butyl-1-oxaspiro[4,5]decane and 13 g (0.11 mol) or 3,5-dimethylpiperidine is stirred at a bath temperature of 140° C. for 16 hours, cooled and taken up in a mixture of diethyl ether and water; the organic phase is separated off, dried over sodium sulphate and concentrated in vacuo and the residue is subjected to a bulb tube distillation (jacket temperature 170° to 200° C. under 0.13 mbar).

9.5 g (57% of theory) of 8-t-butyl-2-(3,5-dimethyl-piperidin-1-yl-methyl)-1-oxaspiro[4,5]decane of refractive index $n_D^{20}$ 1.4869 are obtained.

Preparation of the starting compound

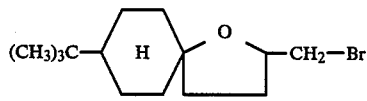

40 g (0.2 mol) of N-bromosuccinimide are added in portions to a solution of 42 g (0.2 mol) of 1-(3-butenyl)-4-t-butyl-cyclohexanol in 600 ml of absolute chloroform, while stirring and cooling, such that the temperature of the reaction mixture does not exceed 40° C. When the addition has ended, the mixture is stirred at room temperature for a further 16 hours, washed twice with water and dried over sodium sulphate and the solvent is removed in vacuo.

43 g (74% of theory) of 2-bromomethyl-8-t-butyl-1-oxaspiro[4,5]decane of refractive index $n_D^{20}=1.4921$ are obtained.

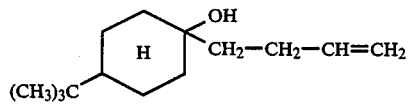

A solution of 45 g (0.3 mol) of 4-t-butylcyclohexanone in 100 ml of absolute tetrahydrofuran is added dropwise to a solution of 7.2 g (0.3 mol) of magnesium and 40.5 g (0.3 mol) of 4-bromo-1-butene in 200 ml of absolute diethyl ether at room temperature, with stirring. When the addition has ended, the mixture is stirred at the reflux temperature for 4 hours and then hydrolyzed with a mixture of 2 normal hydrochloric acid and ice. The organic phase is separated off, dried over sodium sulphate and freed from the solvent in vacuo.

Distillation in vacuo gives 47 g (75% of theory) of 1-(3-butenyl)-4-t-butyl-cyclohexanol of boiling point b.p. 89°–91° C. under 0.1 mbar.

The following aminomethyltetrahydrofurans of the general formula (I) are obtained in a corresponding manner and in accordance with the general statements on the preparation:

$$\text{A} \diagup\!\!\!\diagdown \diagup\!\!\!\diagdown \text{O} \diagdown \text{CH}_2-\text{N} \diagup_{R^2}^{R^1} \quad (I)$$

| Example No. | A $\diagup\!\!\!\diagdown\!\!\!\diagdown$ × | $-\text{N} \diagup_{R^2}^{R^1}$ | physical properties |
|---|---|---|---|
| 2 | 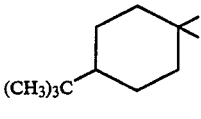 (CH$_3$)$_3$C— | 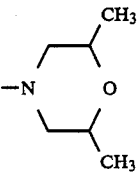 —N with CH$_3$, O, CH$_3$ | $n_D^{20}$ 1.4878 |
| 3 | 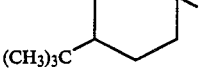 (CH$_3$)$_3$C— |  —N⌒O | $n_D^{20}$ 1.4928 |
| 4 | 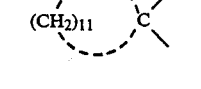 (CH$_2$)$_{11}$ | 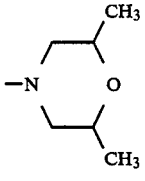 —N with CH$_3$, O, CH$_3$ | $n_D^{20}$ 1.4939 |
| 5 |  (CH$_2$)$_{11}$ | 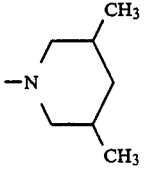 —N with CH$_3$, CH$_3$ | $n_D^{20}$ 1.4983 |
| 6 | 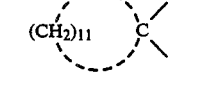 (CH$_2$)$_{11}$ | 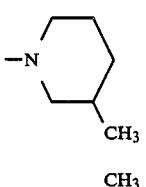 —N with CH$_3$ | $n_D^{20}$ 1.5002 |
| 7 | 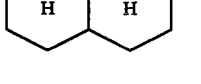 H, H | 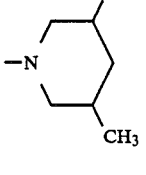 —N with CH$_3$, CH$_3$ | $n_D^{20}$ 1.5190 |
| 8 | 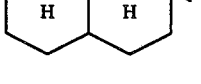 H, H | 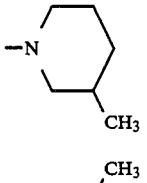 —N with CH$_3$ | $n_D^{20}$ 1.5025 |
| 9 | 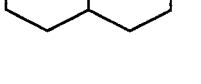 H, H | 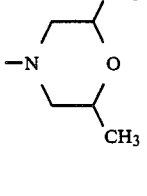 —N with CH$_3$, O, CH$_3$ | $n_D^{20}$ 1.500 |

-continued $$\text{(I)}\quad A \overset{O}{\underset{}{\diagdown\diagup}} CH_2-N \overset{R^1}{\underset{R^2}{\diagdown}}$$

| Example No. | A $\diagdown\diagup$ | $-N\overset{R^1}{\underset{R^2}{\diagdown}}$ | physical properties |
|---|---|---|---|
| 10 | 4-(2-methylbutan-2-yl)-cyclohexyl (CH₃, C₂H₅, CH₃ on C; H) | $-NH-(CH_2)_2-CH_3$ | $n_D^{20}$ 1.4746 |
| 11 | 3,3,5-trimethylcyclohexyl | 3,5-dimethylpiperidino | $n_D^{20}$ 1.4768 |
| 12 | 3,3,5-trimethylcyclohexyl | 3-methylpiperidino | $n_D^{20}$ 1.4759 |
| 13 | 3,3,5-trimethylcyclohexyl | 2,6-dimethylmorpholino | $n_D^{20}$ 1.4713 |
| 14 | 4-(2-methylbutan-2-yl)-cyclohexyl | 2,6-dimethylmorpholino | $n_D^{20}$ 1.4831 |
| 15 | 4-(2-methylbutan-2-yl)-cyclohexyl | 3,5-dimethylpiperidino | $n_D^{20}$ 1.4830 |
| 16 | 4-methylcyclohexyl | 3,5-dimethylpiperidino | $n_D^{20}$ 1.4786 |
| 17 | 4-methylcyclohexyl | 2,6-dimethylmorpholino | $n_D^{20}$ 1.4800 |

-continued $$\text{(I)}$$

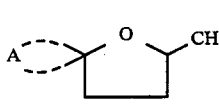

| Example No. | A ⨯ | -N(R¹)(R²) | physical properties |
|---|---|---|---|
| 18 | 4-methyl-4-H cyclohexyl (CH₃, H) | 3-methylpiperidin-1-yl | $n_D^{20}$ 1.4860 |
| 19 | 4-methyl-4-H cyclohexyl | 3,5-dimethylpiperidin-1-yl × saccharin | ¹H—NMR* 4.35–4.5 3.45–3.9 2.8–2.95 |
| 20 | 4-tert-butyl-4-H cyclohexyl | 2,6-dimethylmorpholin-4-yl × saccharin | m.p. 39°–41° C. |
| 21 | 4-tert-butyl-4-H cyclohexyl | 3,5-dimethylpiperidin-1-yl × saccharin | m.p. 37°–39° C. |
| 22 | 4-tert-butyl-4-H cyclohexyl | —NH—(CH₂)₃—O—C₂H₅ | $n_D^{20}$ 1.4734 |
| 23 | 4-tert-butyl-4-H cyclohexyl | —NH—(CH₂)₃—O—C₂H₅ × saccharin | amorphous |
| 24 | 4-tert-butyl-4-H cyclohexyl | —NH—CH₂—CH(OCH₃)₂ | $n_D^{20}$ 1.4610 |

-continued $$\underset{A}{\overset{O}{\diagdown}}\!\!\diagdown\!\!\diagup\!\!\underset{}{\overset{CH_2-N<\!\!\!\overset{R^1}{\underset{R^2}{}}}{}}\qquad (I)$$

| Example No. | A $\diagdown\diagup$ | $-N<\!\!\!\overset{R^1}{\underset{R^2}{}}$ | physical properties |
|---|---|---|---|
| 25 | 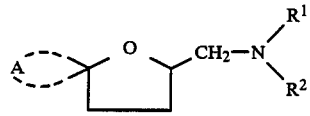 | —NH—CH$_2$—CH(OC$_2$H$_5$)$_2$ | $n_D^{20}$ 1.4650 |
| 26 | 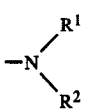 | —NH—(CH$_2$)$_3$—O—(CH$_2$)$_3$—CH$_3$ | $n_D^{20}$ 1.4700 |
| 27 | 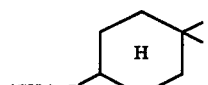 | 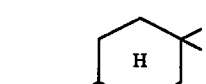 | $n_D^{20}$ 1.4864 |
| 28 | 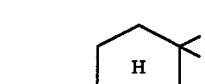 | —NH—CH$_2$—CH(CH$_3$)$_2$ | $n_D^{20}$ 1.4668 |
| 29 | 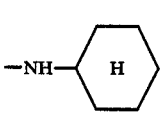 | —NH—CH$_2$—CH(C$_2$H$_5$)$_2$ | $n_D^{20}$ 1.4708 |
| 30 | 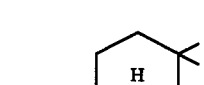 | 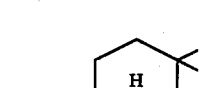 | m.p. 33° C. |
| 31 | 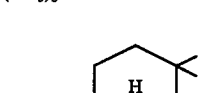 |  | $m_D^{20}$ 1.4784 |
| 32 | 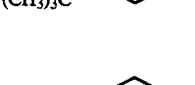 | 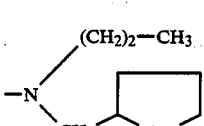 | m.p. −35° C. |

*The $^1$H—NMR spectra were recorded in CDCl$_3$ with tetramethylsilane (TMS) as the internal standard. The chemical shift as the δ value in ppm is stated.

USE EXAMPLES

The compound shown below was employed as the comparison substance in the following use example:

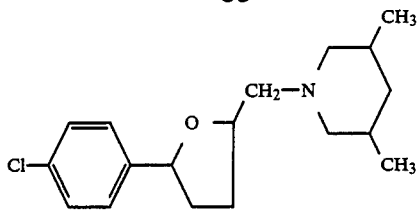

2-(4-Chlorophenyl)-5-(3,5-dimethylpiperidin-1-yl-methyl)tetrahydrofuran
(known from DE-OS (German Published Specification) No. 3,413,996 corresponding to U.S. Pat. No. 4615725).

EXAMPLE A

Erysiphe test (barley)/protective

Solvent: 100 parts by weight of dimethylformamide.
Emulsifier: 0.25 parts by weight of alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, a clearly superior activity compared with the prior art is shown, for example, by the compounds according to the following preparation examples: 1, 2, 3, 4, 7, 8, 9 and 10.

It will be understood that the specification and examples are illustrative but not limitative of the present invention and that other embodiments within the spirit and scope of the invention will suggest themselves to those skilled in the art.

We claim:

1. An aminomethyltetrahydrofuran of the formula

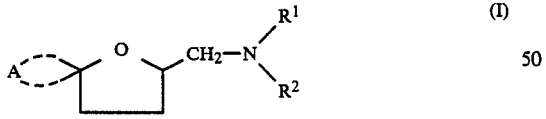

in which

A represents a divalent alkylene or alkenylene chain which completes a mono or bicyclic ring system which is in each case optionally substituted and $R^1$ and $R^2$ independently of one another each represent hydrogen, alkyl, alkenyl, alkinyl, alkoxyalkyl, dialkoxyalkyl, hydroxyalkyl, hydroxyalkoxyalkyl, dioxolanylalkyl, oxolanylalkyl, or dioxanylalkyl, or represent in each case optionally substituted cycloalkylalkyl, cycloalkyl, aralkyl, aralkenyl or aryl, or $R^1$ and $R^2$, together with the nitrogen atom to which they are bonded, represent an optionally substituted saturated heterocyclic radical, which can optionally contain further heteroatoms, or an acid addition salt thereof.

2. An aminomethyltetrahydrofuran or salt according to claim 1, in which

A represents a divalent alkylene or alkenylene chain which has in each case 3 to 18 carbon atoms and is in each case optionally independently substituted by alkyl, alkoxy, alkylthio, alkoxycarbonyl, halogenoalkyl, halogenoalkoxy and halogenoalkylthio with in each case 1 to 9 carbon atoms and if appropriate 1 to 9 identical or different halogen atoms; trialkylsilyl with in each case 1 to 4 carbon atoms in the individual straight-chain or branched alkyl parts; cycloalkylalkyl and cycloalkyl which has in each case 3 to 7 carbon atoms in the cycloalkyl part and if appropriate 1 to 4 carbon atoms in the straight-chain or branched alkyl part and is in each case optionally independently substituted by alkyl with 1 to 4 carbon atoms or halogen; in each case divalent alkylene or alkenylene which has in each case up to 5 carbon atoms and is in each case optionally independently substituted by alkyl, halogenoalkyl, alkoxy and halogenoalkoxy with in each case 1 to 4 carbon atoms and if appropriate 1 to 9 identical or different halogen atoms or halogen, and monovalent aryl or divalent arylene which has in each case 6 to 10 carbon atoms and is in each case optionally indepently substituted by halogen, cyano, nitro and in each case straight-chain or branched alkyl, alkoxy, alkylthio, halogenoalkyl, halogenoalkoxy, halogenoalkylthio, alkoxycarbonyl and alkoximinoalkyl with in each case 1 to 4 carbon atoms in the individual alkyl parts and if appropriate 1 to 9 identical or different halogen atoms, and $R^1$ and $R^2$ independently of one another each represent hydrogen; or represent in each case straight-chain or branched alkyl with 1 to 12 carbon atoms, alkenyl with 3 to 8 carbon atoms, alkinyl with 3 to 8 carbon atoms, hydroxyalkyl with 2 to 6 carbon atoms, alkoxyalkyl or dialkoxyalkyl with in each case 1 to 6 carbon atoms or hydroxyalkoxyalkyl with 2 to 6 carbon atoms in the individual alkyl parts, or represent in each case straight-chain or branched dioxolanylalkyl, oxolanylalkyl or dioxanylalkyl with in each case 1 to 4 carbon atoms in the alkyl part, or represent cycloalkyl or cycloalkylalkyl which has in each case 3 to 7 carbon atoms in the cycloalkyl part and if appropriate 1 to 4 carbon atoms in the alkyl part and is in each case optionally independently substituted in the cycloalkyl part by halogen and in each case stright-chain or branched alkyl, alkoxy, halogenoalkyl and halogenoalkoxy with in each case 1 to 4 carbon atoms and if appropriate 1 to 9 identical or different halogen atoms; or furthermore represent arylalkyl, arylalkenyl or aryl which has in each case 6 to 10 carbon atoms in the aryl part and if appropriate up to 6 carbon atoms in the straight-chain or branched alkyl or alkenyl part and is in each case optionally independently substituted in the aryl part by halogen, cyano, nitro and in each case stright-chain or branched alkyl, alkoxy, alkylthio, halogenoalkyl, halogenoalkoxy, halogenoalkylthio, alkoxycarbonyl and alkoximinoalkyl with in each case 1 to 4 carbon atoms in the individual alkyl parts and if appropriate 1 to 9 indentical or different halogen atoms, or $R^1$ and $R^2$, together with the nitrogen atom to which they are bonded, represent a saturated 5- to 7-membered heterocyclic radical which is optionally mono- or polysubstituted by identical or different substituents and can optionally contain a further heteroatom.

3. An aminomethyltetrahydrofuran or salt according to claim 1, in which

A represents 1,4-butylene, 1,5-pentylene, 1,6-hexylene, 1,5-pent-1-enylene, 1,5-pent-2-enylene or 1,11-undecyclene, in each case optionally mono- or independently di-, tri-, tetra- or pentasubstituted by methyl, ethyl, n- or i-propyl, n-, i-, s- or t-butyl, n- or i-pentyl, n- or i-hexyl, n- or i-heptyl, n- or i-octyl, n- or i-nonyl, methoxy, ethoxy, n- or i-propoxy, n-, i-, s- or t-butoxy, methylthio, methoxycarbonyl, ethoxycarbonyl, trifluoromethyl, trifluoromethoxy, trifluoromethylthio and trimethylsilyl, cyclohexyl, cyclohexylmethyl, cyclohexylethyl and cyclohexylpropyl, in each case optionally mono-, di- or tri- substituted by identical or different substituents from the group consisting of fluorine, chlorine, bromine, methyl, ethyl, n- or i-propyl and/or t-butyl, methylene, 1,2-ethylene, 1,3-propylene, 1,4-butylene and 1,4-butenylene, in each case optionally mono-, di- or trisubstituted by identical or different substituents from the group consisting of methyl, ethyl, n- or i-propyl, n-, i-, s- or t-butyl, trifluoromethyl and trifluoromethoxy, and phenyl and o-phenylene, in each case optionally mono-, di- or trisubstituted by identical or different substituents from the group consisting of fluorine, chlorine, bromine, cyano, nitro, methyl, ethyl, n- or i-propyl, n-, i-, s- or t-butyl, methoxy, ethoxy, trifluoromethyl, trifluoromethoxy, trifluoromethylthio and methoximinomethyl, and $R^1$ and $R^2$ independently of one another each represent hydrogen, methyl, ethyl, n- or i-propyl, n-, i-, s- or t-butyl, n- or i-pentyl, n- or i-hexyl, n- or i-heptyl, n- or i-octyl, allyl, n- or i-butenyl, n- or i-pentenyl, propargyl, n- or i-butenyl, n- or i-pentenyl, propargyl, n- or i-butinyl, hydroxyethyl, hydroxypropyl, methoxyethyl, ethoxyethyl, propoxyethyl, butoxyethyl, methoxypropyl, ethoxypropyl, propoxypropyl, butoxypropyl, hydroxyethoxyethyl, dimethoxyethyl, dimethoxypropyl, diethoxyethyl, dioxolanylmethyl, dioxolanylethyl, oxolanylmethyl, oxolanylethyl, dioxanylmethyl or dioxanylethyl, or represent cyclopropyl, cyclopropylmethyl, cyclopropylethyl, cyclopropylpropyl, cyclopentyl, cyclopentylmethyl, cyclohexyl or cyclohexylmethyl, in each case optionally mono-, di-, tri-, tetra- or pentasubstituted by identical or different substituents from the group consisting of fluorine, chlorine, bromine, methyl, ethyl, n- or i-propyl and n-, i-, s- and/or t-butyl, or represent phenyl, benzyl or phenethyl, in each case optionally mono-, di- or trisubstituted by identical or different substituents, from the group consisting of fluorine, chlorine, bromine, cyano, nitro, methyl, ethyl, n- or i-propyl, n-, i-, s- or t-butyl, methoxy, ethoxy, methylthio, trifluoromethyl, trifluoromethoxy, trifluoromethylthio, methoxycarbonyl, ethoxycarbonyl and methoximinomethyl, or $R^1$ and $R^2$, together with the nitrogen atom to which they are bonded, represent a heterocyclic radical of the formula

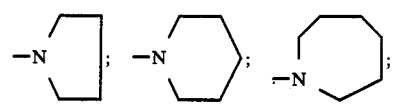

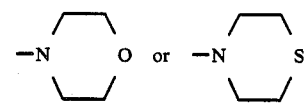

which is optionally mono-, di- or trisubstituted by indentical or different substituents from the group consisting of methyl, ethyl and hydroxymethyl.

4. An aminomethyltetrahydrofuran according to claim 1, in which

A, together with the carbon atom to which it is bonded, represents a carbocyclic ring system of the formula

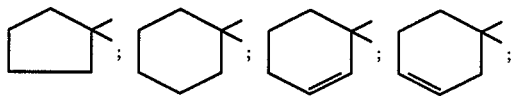

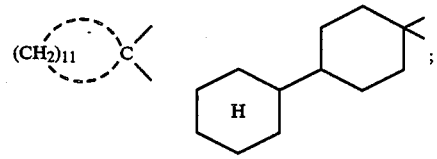

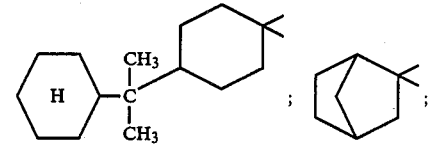

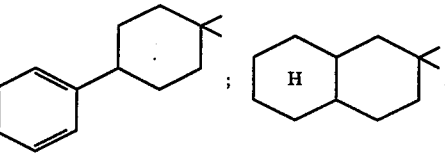

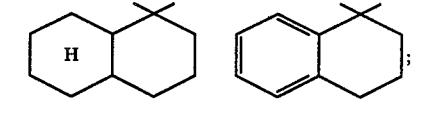

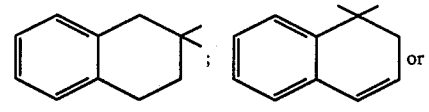

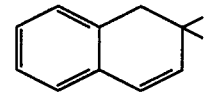

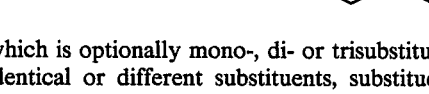

which is optionally mono-, di- or trisubstituted by identical or different substituents, substituents in the cycloaliphatic rings being selected from methyl, ethyl, n- or i-propyl, n- i-, s- or t-butyl, n- or i-pentyl, trifluoromethyl, trifluoromethoxy, methoxycarbonyl, ethoxycarbonyl and trimethylsilyl, and substituents in the aromatic rings being selected from fluorine, chlorine, bromine, methyl, ethyl, n- or i-propyl, n-, i-, s- or t-butyl, methoxy, ethoxy, trifluoromethyl, trifluoromethoxy and trifluoromethylthio, and R¹ and R² independently of one another each represent hydrogen, methyl, ethyl, n- or i-propyl, n-, i-, s- or t-butyl, n- or i-pentyl, n- or i-hexyl, allyl, n- or i-butenyl, n- or i-pentenyl, propargyl, n- or i-butinyl, hydroxyethyl, hydroxypropyl, methoxyethyl, methoxypropyl, ethoxyethyl, ethoxypropyl, hydroxyethoxyethyl, dimethoxyethyl, diethoxyethyl, dioxolanylmethyl, dioxolanylethyl, oxolanylmethyl, oxolanylethyl, dioxanylmethyl, cyclopropylmethyl, dichlorocyclopropylmethyl, dimethylcyclopropylmethyl, dichlorodimethycyclopropylmethyl, cyclopentyl, cyclohexyl or cyclohexylmethyl, or R¹ and R², together with the nitrogen atom to which they are bonded, represent a heterocyclic radical of the formula

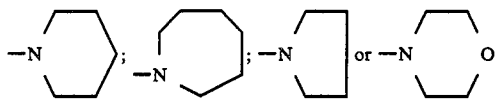

which is optionally mono-, di- or trisubstituted by identical or different substituents selected from the group consisting of methyl, ether and hydroxymethyl.

5. A compound according to claim 1, wherein such compound is 8-t-butyl-2-(3,5-dimethylpiperidin-1-yl-methyl)-1-oxaspiro[4,5decane of the formula

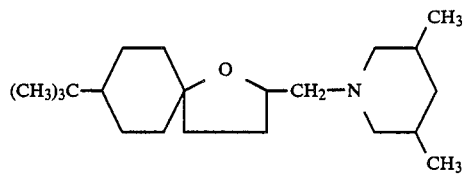

or an acid addition salt thereof.

6. A compound according to claim 1, wherein such compound is 8-t-butyl-2-(2,6-dimethylmorpholin-4-yl-methyl)-1-oxaspiro[4,5]decane of the formula

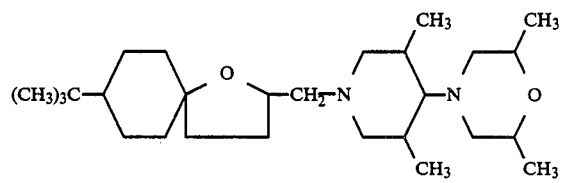

or an acid addition salt thereof.

7. A fungicidal composition comprising a fungicidally effective amount of a compound or salt according to claim 1, and a diluent.

8. A method of combating fungi which comprises applying to such fungi or to a fungus habitat a fungicidally effective amount of a compound or salt according to claim 1.

9. The method according to claim 1, wherein such compound is
8-t-butyl-2-(3,5-dimethylpiperidin-1-yl-methyl)-1-oxaspiro[4,5]decane or
8-t-butyl-2-(2,6-dimethylmorpholin-4-yl-methyl)-1-oxaspiro[4,5]decane
or an acid addition salt thereof.

* * * * *

UNITED STATES PATENT AND TRADEMARK OFFICE
CERTIFICATE OF CORRECTION

PATENT NO. : 4,800,202

DATED : January 24, 1989

INVENTOR(S) : Joachim Weissmüller, et al

It is certified that error appears in the above-identified patent and that said Letters Patent is hereby corrected as shown below:

| | |
|---|---|
| Col. 26, line 15 | Delete "or" and substitute --of-- |
| Col. 36, line 62 | Correct --straight-- |
| Col. 36, line 67 and Col. 38, line 14 | Correct --identical-- |
| Col. 39, line 33 | Delete "ether" and substitute --ethyl-- |

Signed and Sealed this

Twelfth Day of December, 1989

*Attest:*

JEFFREY M. SAMUELS

*Attesting Officer*   *Acting Commissioner of Patents and Trademarks*